United States Patent
Cunningham et al.

[11] Patent Number: 6,063,039
[45] Date of Patent: May 16, 2000

[54] METHOD AND APPARATUS FOR OBTAINING BLOOD FOR DIAGNOSTIC TESTS

[75] Inventors: David D. Cunningham, Lake Villa; Timothy P. Henning, Vernon Hills; Eric B. Shain, Glencoe; Douglas F. Young, Grayslake, all of Ill.

[73] Assignee: Abbott Laboratories, Abbott Park, Ill.

[21] Appl. No.: 08/759,698

[22] Filed: Dec. 6, 1996

[51] Int. Cl.⁷ .................................................. A61B 10/00
[52] U.S. Cl. ........................... 600/573; 600/583; 604/317
[58] Field of Search .................................... 600/562, 573, 600/583, 584, 578, 579; 604/317, 318

[56] References Cited

U.S. PATENT DOCUMENTS

| | | |
|---|---|---|
| Re. 32,922 | 5/1989 | Levin et al. . |
| 1,934,046 | 11/1933 | Demarchi . |
| 3,815,579 | 6/1974 | Rose ........................................ 600/573 |
| 4,203,446 | 5/1980 | Hofert et al. . |
| 4,360,016 | 11/1982 | Sarrine . |
| 4,627,445 | 12/1986 | Garcia et al. . |
| 4,637,403 | 1/1987 | Garcia et al. . |
| 4,653,513 | 3/1987 | Dombrowski . |
| 4,775,361 | 10/1988 | Jacques et al. . |
| 4,844,098 | 7/1989 | Mitchen . |
| 4,990,154 | 2/1991 | Brown et al. . |
| 5,054,499 | 10/1991 | Swierczek . |
| 5,161,532 | 11/1992 | Joseph . |
| 5,165,418 | 11/1992 | Tankovich . |
| 5,320,607 | 6/1994 | Ishibashi . |
| 5,368,047 | 11/1994 | Suzuki et al. . |
| 5,374,556 | 12/1994 | Bennett et al. . |
| 5,487,748 | 1/1996 | Marshall et al. . |
| 5,509,410 | 4/1996 | Hill et al. . |
| 5,554,153 | 9/1996 | Costello et al. . |
| 5,569,223 | 10/1996 | Wandell et al. . |
| 5,662,127 | 9/1997 | De Vaughn . |
| 5,680,872 | 10/1997 | Sesekura et al. . |
| 5,730,714 | 3/1998 | Guy et al. .................................. 604/20 |

FOREIGN PATENT DOCUMENTS

| | | |
|---|---|---|
| 30566/84 | 7/1984 | Australia . |
| 0 367 752 | 5/1990 | European Pat. Off. . |
| 0 453 283 | 10/1991 | European Pat. Off. . |
| 0 595 237 | 5/1994 | European Pat. Off. . |
| 2 574299 | 6/1986 | France . |
| 2 577 808 | 8/1986 | France . |
| 242 962 | 2/1987 | German Dem. Rep. . |
| 2803345 | 6/1979 | Germany . |
| 3 708 031 | 11/1987 | Germany . |
| 3 806 574 | 9/1989 | Germany . |
| 2 222 251 | 2/1990 | United Kingdom . |
| WO 87/00413 | 1/1987 | WIPO . |
| WO 92/02175 | 2/1992 | WIPO . |
| WO 94/09713 | 5/1994 | WIPO . |
| 9637148 | 11/1996 | WIPO . |

OTHER PUBLICATIONS

Lane, et al., "Ultraviolet–Laser Ablation of Skin", IBM Research Report (1984).

*Primary Examiner*—Cary O'Connor
*Assistant Examiner*—Pamela Wingood
*Attorney, Agent, or Firm*—David L. Weinstein

[57] ABSTRACT

Method and apparatus for obtaining a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of a vacuum and a stretching of the skin.

In another aspect of the invention, an apparatus for carrying out the method described previously is provided. The apparatus comprises:

(a) a device for forming an unobstructed opening in an area of skin from which said sample is to be extracted, preferably a lancing assembly; and (b) a vacuum pump.

Preferably, the apparatus also includes a housing.

58 Claims, 2 Drawing Sheets

METHOD AND APPARATUS FOR OBTAINING BLOOD FOR DIAGNOSTIC TESTS

BACKGROUND OF THE INVENTION

1. Field of the Invention

This invention relates to a method and apparatus for obtaining samples of blood for diagnostic purposes.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

The medical apparatus of the prior art for monitoring the level of glucose in the blood stream required that an individual have separately available a needle or lancet for extracting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by extracting blood via lancet at a different body site. The finger lancet presents another problem because of the limited area available on the fingers for lancing. Because it is recommended that diabetics monitor their blood glucose levels four to six times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin. See also U.S. Pat. No. 5,320,607, which discloses a device comprising a sealed vacuum chamber in a state of preexisting reduced pressure, a support member for the sealed vacuum chamber, the support member defining a suction portion adjacent the sealed vacuum chamber, the suction portion, in cooperation with the sealed vacuum chamber, exposing an area of the skin of a patient to a reduced pressure state when the device is actuated, and means arranged within the suction portion for slightly rupturing a portion of the area of skin of the patient exposed to the reduced pressure state.

Because the blood volume requirements for a standard glucose test strip is typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids could be found if a reliable method were found for lancing a body part that is less sensitive to pain than the finger and obtaining a useful amount of blood from that body part. A body part such as the forearm is much less sensitive to pain than the finger, but the amount of blood resulting from the lancing procedure is generally of an inadequate volume for use with current detection technology. Ways of increasing blood flow to the finger are common knowledge. The recommendation is made to diabetics to run their finger under hot water prior to lancing to improve the blood flow in the finger and the amount of blood collected from the finger. Running hot water over a body part to improve blood flow is impractical for areas such as the forearm or thigh. The availability of hot water is also a concern.

It would be desirable to develop a technique and apparatus for obtaining blood for diagnostic purposes in a painless, reliable manner.

SUMMARY OF THE INVENTION

This invention provides a method and apparatus for extracting a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of vacuum and stretching of the skin.

In a preferred embodiment of the method, step (a) is preceded by the step of increasing the availability of blood in the portion of the skin from which the sample is to be extracted. In this preferred embodiment, the availability of blood in the portion of the skin from which the sample is to be extracted can be increased by means of a vacuum, which is applied to the surface of the skin in the vicinity of the opening prior to forming the opening in the skin. The vacuum causes the portion of the skin in the vicinity of the blood extraction site to become engorged with blood. The vacuum also causes the portion of the skin in the vicinity of the blood extraction site to become stretched. An opening in this stretched portion of skin can be formed with a cutting or puncturing device, e.g., a lancet, or other device capable of forming an opening in the skin, e.g., a laser or a fluid jet. If a cutting or puncturing device is used to form the opening, it must be retracted from the opening prior to the step of extracting the sample of blood from the opening. This retraction will allow the unrestricted flow of blood through the opening. After the opening is formed, a vacuum is used to aid in extracting the sample of blood from the opening in the skin. The sample can be analyzed from the drops of blood that collect on the surface of the skin at the site of the opening by applying the blood directly to a glucose detector. It is preferred, however, that the sample be collected in such a manner, e.g., via a capillary tube, that it can be analyzed by conventional diagnostic devices, such as, for example, a biosensor. In another preferred embodiment, the sample can be collected in a collection zone that is integrated with a conventional diagnostic device, e.g., a biosensor.

In an alternative of the aforementioned preferred embodiment, the availability of blood in the area of the skin from which the sample is to be extracted can be increased by means of applying thermal energy to that area of skin. The thermal energy causes the blood in that area of the skin to flow more rapidly, thereby allowing more blood to be collected per given unit of time. In this alternative embodiment, steps (a) and (b) can be carried out in the same manner as they were carried out in the aforementioned preferred embodiment.

In another aspect of the invention, an apparatus for collecting a sample of body fluid for analysis in a diagnostic test, e.g., blood, is provided. In a preferred embodiment, the apparatus comprises:

(a) a housing;
(b) a device for forming an unobstructed opening in an area of skin from which said sample is to be extracted, preferably a lancing assembly; and
(c) a vacuum pump.

It is also possible to dispense with the housing. However, the housing is preferred for the convenience of the patient and the protection of the components.

The vacuum pump requires a source of power. If the apparatus includes a housing, the source of power can be disposed within the housing. Alternatively, the source of power can be external to the housing.

The preferred device for forming an unobstructed opening in the area of the skin from which the sample of blood is to be extracted is a lancing assembly, which comprises a lancet for forming an opening in the skin. Alternatively, the unobstructed opening in the skin can be formed by a laser or a fluid jet.

The vacuum pump can serve the dual purposes of (1) stretching the skin and (2) enhancing the extraction of the sample of blood from the unobstructed opening in the skin. Preferably, the vacuum pump can serve the triple purposes of (1) stretching the skin, (2) increasing the availability of blood to the area of the skin from which the sample is to be extracted, and (3) enhancing the extraction of the sample of blood from the unobstructed opening in the skin. Preferably, the housing further contains electronics having programmed instructions to switch the vacuum pump on and off to maintain the desired level of vacuum.

The apparatus preferably contains valves, such as, for example, solenoid valves, for triggering the lancet of the lancing assembly and releasing the vacuum at the conclusion of the blood extraction procedure. The apparatus can optionally contain a heating element to increase the availability of blood to the area of the skin from which the sample is to be extracted. The apparatus can also contain a glucose detector integrated with the apparatus, e.g., a biosensor, to analyze the sample of blood collected by the apparatus.

The method and apparatus of this invention provide several advantages over the methods and apparatus of the prior art. First, a sufficient amount of blood can be extracted from parts of the body, other than the finger, for conducting glucose monitoring tests. Second, by rendering other parts of the body suitable for extracting blood, the use of a painful finger lance can be avoided. Third, by increasing the availability of blood at the site where the blood is to be extracted, the period of time required for extracting the sample can be reduced. Because of these advantages, the diabetic patient is more likely to monitor glucose levels in the blood at the intervals prescribed by his doctor.

BRIEF DESCRIPTION OF THE DRAWINGS

FIG. 2 also illustrates the spatial relationship between the nosepiece of lancing assembly and a glucose detector, e.g., a biosensor.

DETAILED DESCRIPTION

Figure 1:
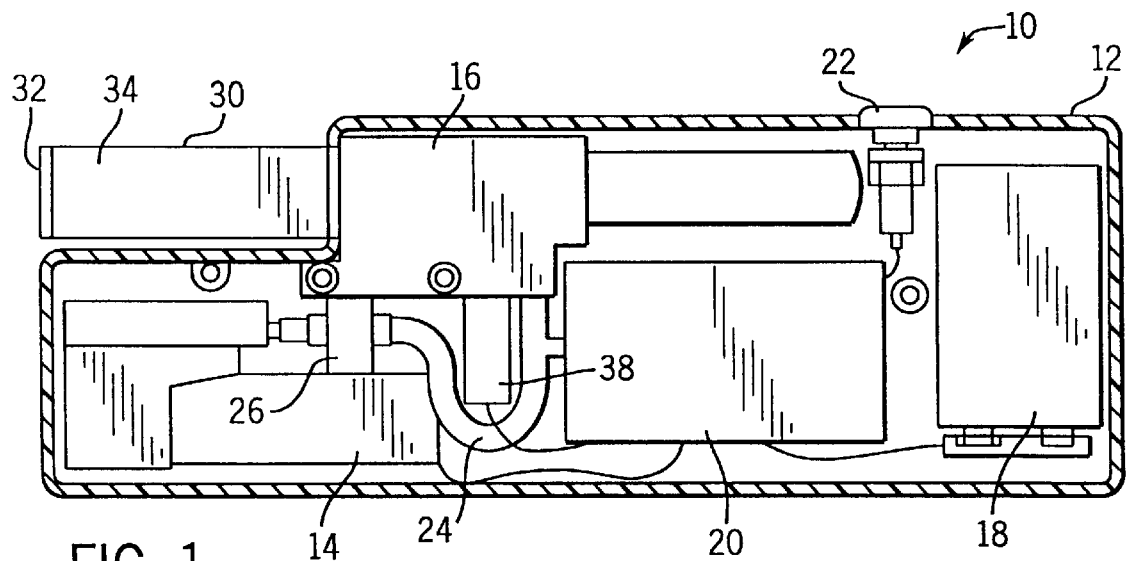
FIG. 1 is a plan view of the components of a preferred embodiment of the apparatus of this invention. In this Figure, the cover of the housing is removed.

The embodiments of this invention require the following steps to carry out the function of obtaining a sample of blood for carrying out a diagnostic test, e.g., glucose monitoring:

(a) forming an unobstructed opening in the area of the skin from which the sample of blood is to be extracted; and
(b) extracting the sample of blood from the unobstructed opening in the skin, with the aid of a vacuum and a stretching of the skin.

The step of forming an unobstructed opening in the area of the skin from which the sample of blood is to be extracted is carried out by a piercing device or some other type of device capable of forming an unobstructed opening in the skin. Piercing devices suitable for this invention include, but are not limited to, mechanical lancing assemblies. Other type of device capable of forming an unobstructed opening in the skin include, but are not limited to, lasers and fluid jets. Other types of devices capable of forming an unobstructed opening in the skin can be used, and this disclosure should not be construed so as to be limited to the devices listed. Mechanical lancing assemblies are well-known in the art. These assemblies comprise include standard steel lancets, serrated devices, and multiple tip devices. The lancets can be made from metal or plastic. Multiple tip devices provide redundancy, which can reduce the number of failures and increase the volume of blood extracted.

Lasers suitable for forming an unobstructed opening in the skin to draw blood are also well-known in the art. See for example, U.S. Pat. Nos. 4,775,361, 5,165,418, 5,374,556, International Publication Number WO 94/09713, and Lane et al. (1984) IBM Research Report—"Ultraviolet-Laser Ablation of Skin", all of which are incorporated herein by reference. Lasers that are suitable for forming an unobstructed opening in the skin the skin include Er:YAG, Nd:YAG, and semiconductor lasers.

Fluid jets suitable for forming an unobstructed opening in the skin employ a high pressure jet of fluid, preferably a saline solution, to penetrate the skin.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be extracted", "unobstructed opening in the skin", and the like are intended to mean that the portion of the opening below the surface of the skin is free from any foreign object that would clog, hamper, block, or close up the opening, such as, for example, a needle of any type. For example, if a lancet is used to form the opening, it must be retracted from the opening prior to the commencement of the extraction of blood. Because lasers and fluid jets do not require contact with the skin to form openings in the skin, these types of devices typically provide unobstructed openings. However, these expressions are not intended to include foreign objects at the surface of the skin or above the surface of the skin, such as, for example, a glucose monitor. This feature, i.e., the unobstructed opening, can be contrasted with the opening used in the method and apparatus described in U.S. Pat. No. 5,320,607, in which the piercing and cutting means remains in the skin during the duration of the period of blood extraction. By leaving the opening unobstructed, blood can be extracted much more rapidly from the opening than it would be extracted if the piercing and cutting means were allowed to remain in the opening. In addition, the requirement of an unobstructed opening exposes the body to a foreign object either not at all or for only a very short period of time, which is welcomed by the patient.

The step of extracting the sample of blood from the opening in the skin is carried out by a combination of extraction enhancing elements. Extraction enhancing elements suitable for use in this invention include, but are not limited to, vacuum, skin stretching elements, and heating elements. It has been discovered that when these elements are used in combination, the volume of blood extracted is greatly increased, particularly when a vacuum is applied in combination with skin stretching. In this combination, the vacuum not only causes the blood to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e.g., stretching of the skin.

In the preferred embodiment of this invention, step (a), the step of forming the unobstructed opening, is preceded by the step of increasing the availability of blood at the area of the skin from which the sample is to be extracted. The availability of blood at a given area of the skin can be increased by at least two methods. In one method, a vacuum can be used to cause blood flowing through blood vessels to pool in the area of the skin where the vacuum is applied. In another method, heat can be used to cause blood flowing through blood vessels to flow more rapidly in the area of the skin where heat is applied, thereby allowing a greater quantity of blood to be extracted from the blood extraction site per unit of time. Although the step of increasing the availability of blood in the vicinity of the blood extraction site is not required, the employment of this step can result in a greater volume of blood extracted. Elements for increasing the availability of blood at a blood extraction site that are suitable for use in this invention include, but are not limited to, vacuum, localized heating element, skin stretching element, and chemicals. As stated previously, applying a vacuum to the area of the skin from which blood is to be extracted can increase blood availability under and within the skin at the application site. The vacuum can also be used to stretch the skin upwardly into a chamber, thereby increasing pooling of blood under and within the skin. This combination of vacuum and skin stretching can be an extension of the combination used to extract blood from the opening in the skin, as previously described. It is well-known that heat can increase perfusion on the large scale of a limb or a finger. Chemical means, such as histamine, can be used to cause a physiological response to increase perfusion under and within the skin.

In the preferred embodiments of the invention, the extracted blood is also collected. The step of collecting the sample of blood can be carried out in a variety of ways. For example, the blood can be collected in capillary tubes or absorbent paper. Alternatively, the blood can be allowed to remain in the lancet assembly, from which it can used directly in a diagnostic test. Most preferably, the sample of blood is collected on the application zone of a glucose detector, from where it can be used directly to provide an indication of the concentration of glucose in the blood. Regardless of the manner in which the blood sample is collected, the sample can be analyzed at a time later than the time of collection or at a location remote from the location of collection or both.

A preferred embodiment of the invention will now be described in detail. Blood extraction device 10 comprises a housing 12. Disposed within the housing 12 are a vacuum pump 14, a lancing assembly 16, a battery 18, and electronics 20. A switch 22 is provided to activate electronics 20.

The housing 12 is preferably made from a plastic material. It is preferably of sufficient size to contain all of the components that are required for forming an unobstructed opening in the area of the skin from which the sample of blood is to be extracted, extracting the sample of blood from the unobstructed opening in the skin, preferably with the aid of a vacuum and a stretching of the skin, and collecting the extracted sample in an amount sufficient to carry out a diagnostic test. Methods of preparing the housing 12 are well-known to one of ordinary skill in the art. As stated previously, the housing 12 is not required, but is preferred for the convenience of the patient and the protection of the components.

The vacuum pump 14 must be capable of providing a vacuum that will provide sufficient suction to stretch the portion of the skin in the region from which the sample of blood is to be extracted. Typically, the portion of stretched skin is raised a distance of 1 to 10 mm, preferably 3 to 5 mm, from the plane of the body part of which it is a portion. As the suction provided by the vacuum pump 14 is stretching the appropriate portion of skin, the suction provided by the vacuum pump 14 also causes the stretched portion to become engorged with blood. The level of suction provided must be sufficient to cause a relatively large volume of blood to become engorged at the point that the vacuum is applied. The vacuum pump 14 must also be capable of providing sufficient suction to extract blood from the opening in the skin at a rate sufficient to extract at least 1 $\mu$L of blood within a period of five minutes. A vacuum pump 14 that is suitable for the device of this invention can be a diaphragm pump, a piston pump, a rotary vane pump, or any other pump that will perform the required functions set forth previously. Typically, the vacuum pump 14 employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump 14 is preferably capable of providing a pressure of down to about −14.7 psig, and is more preferably operated at from about −3.0 psig to about −10.0 psig. The area of the skin subjected to vacuum preferably ranges up to about 50 cm$^2$, more preferably from about 0.1 to about 5.0 cm$^2$. The period of vacuum application prior to forming the opening in the skin, i.e., for increasing the availability of blood to the application site, preferably ranges up to about 5 minutes, preferably from about 1 to about 15 seconds. The period of vacuum application subsequent to forming the opening in the skin, i.e., for aiding in the extraction of blood from the unobstructed opening, preferably ranges up to about 5 minutes, preferably from about 1 to about 60 seconds. The vacuum provided by the vacuum pump 14 can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The vacuum pump feature offers significant advantages over the method and apparatus described in U.S. Pat. No. 5,320,607, in which a sealed vacuum chamber in a state of preexisting reduced pressure is used. The use of a vacuum pump provides the user with greater control of blood extraction conditions than does a sealed vacuum chamber in a state of preexisting reduced pressure. For example, if the vacuum is insufficient, energy can be provided to the vacuum pump to bring about a higher level of vacuum, thereby providing greater suction.

The lancing assembly 16 comprises at least one lancet. Standard lancets can be used in the lancing assembly of this invention. Narrow gauge (28 to 30 gauge) lancets are preferred. Lancets suitable for this invention can be made from metal or plastic. Lancets suitable for this invention can have single points or multiple points. The depth of penetration of the lancet preferably ranges from about 0.4 to about 2.5 mm, more preferably from about 0.4 to about 1.6 mm. The length of the lancet or lancets preferably ranges from about 1 mm to about 5 mm. The lancing assembly is preferably located so that the user can easily replace used lancets. The lancet of the lancing assembly 16 can be cocked manually or automatically, e.g., by means of a vacuum-actuated piston or diaphragm. The lancet of the lancing assembly 16 can be triggered by manually or automatically, e.g., by means of a vacuum-actuated piston or diaphragm.

Lancing assemblies are well-known in the art. Representative examples of lancing assemblies suitable for this invention are described in U.S. Pat. Nos. Re. 32,922, 4,203,446, 4,990,154, and 5,487,748, all of which are incorporated herein by reference. A particularly suitable lancing assembly for this invention is described in U.S. Pat. No. Re. 32,922. However, any lancing assembly selected should operate in conjunction with the other features of the apparatus of this invention. For example, if a vacuum is employed, the lancing assembly must be designed so that a vacuum can be formed and drawn through the assembly. The lancing assembly can be designed to allow automatic cocking and automatic triggering of the lancet.

The vacuum pump 14 is connected to the lancing assembly 16 by an evacuation assembly 24. The air that is evacuated from the lancing assembly 16 by the vacuum pump 14 is removed via the evacuation assembly 24. The evacuation tube 24 is typically made from a polymeric material. A check valve 26 is placed between the vacuum pump 14 and the lancing assembly 16 at a point in the evacuation tube 24 to prevent air removed from the lancing assembly 16 by the vacuum pump 14 from flowing back to the lancing assembly 16 and adversely affecting the vacuum.

A source of power for the vacuum pump 14 can be disposed within the housing 12. A source of power suitable for the device of this invention is a battery 18. Alternatively, an external source of power can be used to operate the vacuum pump 14. The power source is actuated by the electronics 20, which, in turn, is actuated by the switch 22.

The electronics 20 may incorporate a microprocessor or microcontroller. The function of the electronics 20 is to switch power on and off to operate the various components in the apparatus. These components include, but are not limited to, the vacuum pump 14. The electronics 20 can also be use to switch power on and off to operate components in alternative embodiments, e.g., heating elements, lancets, indicating devices, and valves. Electronics suitable for this invention is the "TATTLETALE MODEL 5F" controller/data logger, commercially available from Onset Computer Corporation, 536 MacArthur Blvd.

P. O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available. Auxiliary electronic devices suitable for use in this invention include the following components:

| Component | Source | Catalog Number |
|---|---|---|
| Mosfet Drivers | International Rectifier El Segundo, CA | IRLD024 |
| Op-Amp | National Semiconductor Santa Clara, CA | LM358 |
| Status LED | Hewlett-Packard Newark Electronics Schaumburg, IL | HLMPD150 |
| Pressure Sensor | Sensym, Inc. Milpitas, CA | SDX15D4 |

Figure 3:
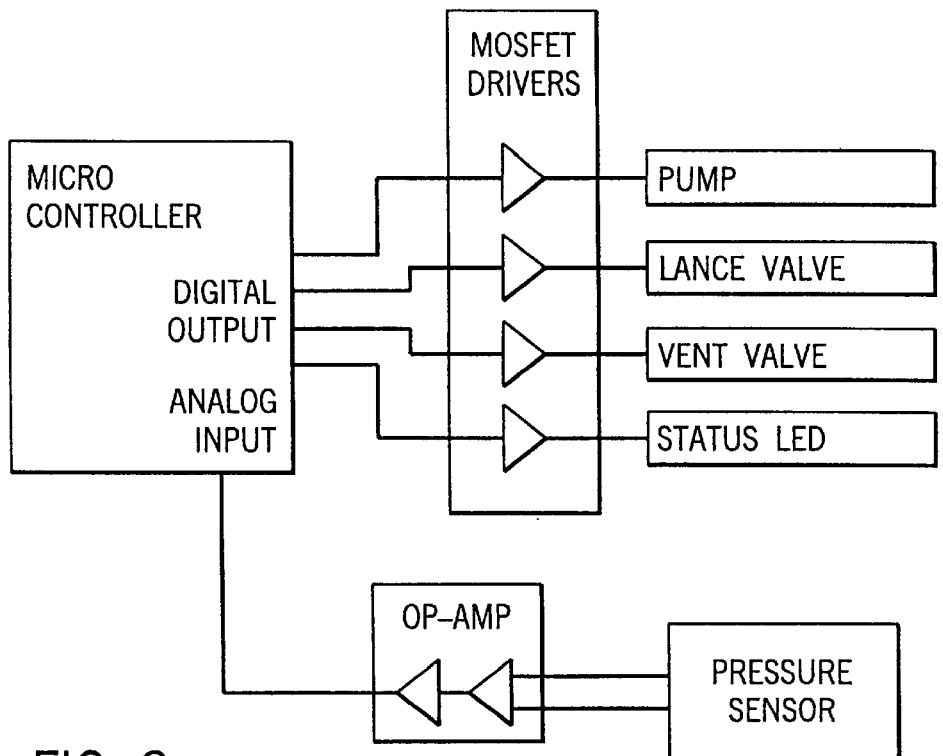
FIG. 3 is a block diagram illustrating the electronics of the preferred embodiment.

FIG. 3 illustrates by way of a block diagram how the foregoing electronic components can be arranged to carry out the method of the present invention.

Figure 2:
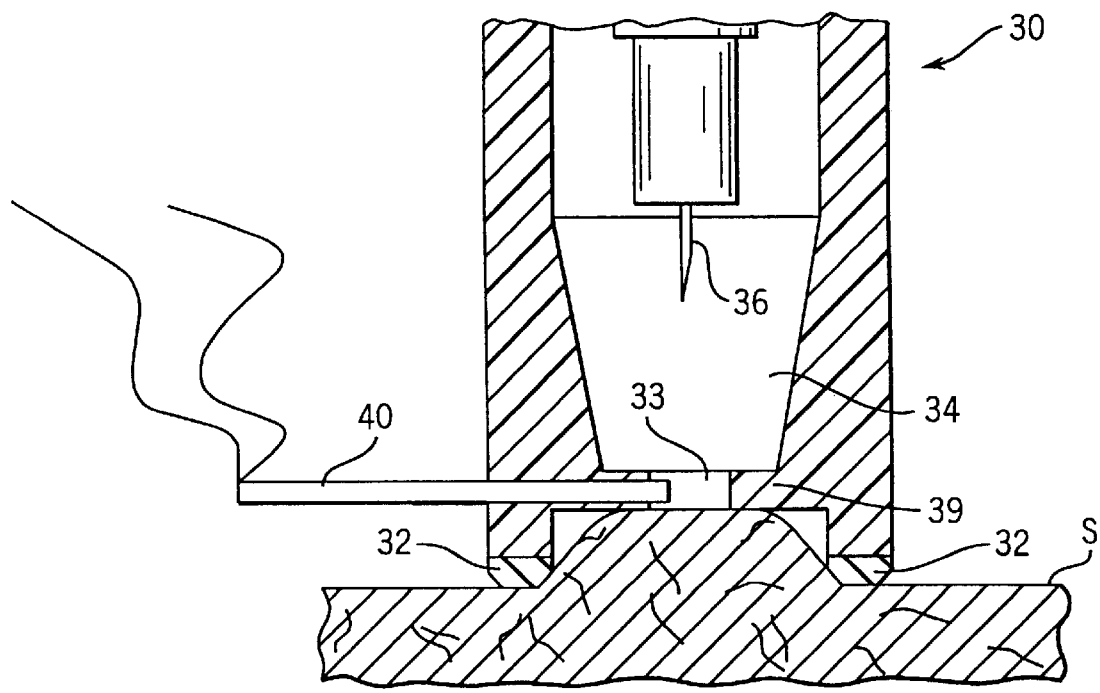
FIG. 2 is a schematic diagram illustrating how a vacuum causes a portion of the skin to become stretched prior to the formation of an opening in the skin from which the sample of blood is extracted.
Figure 4:
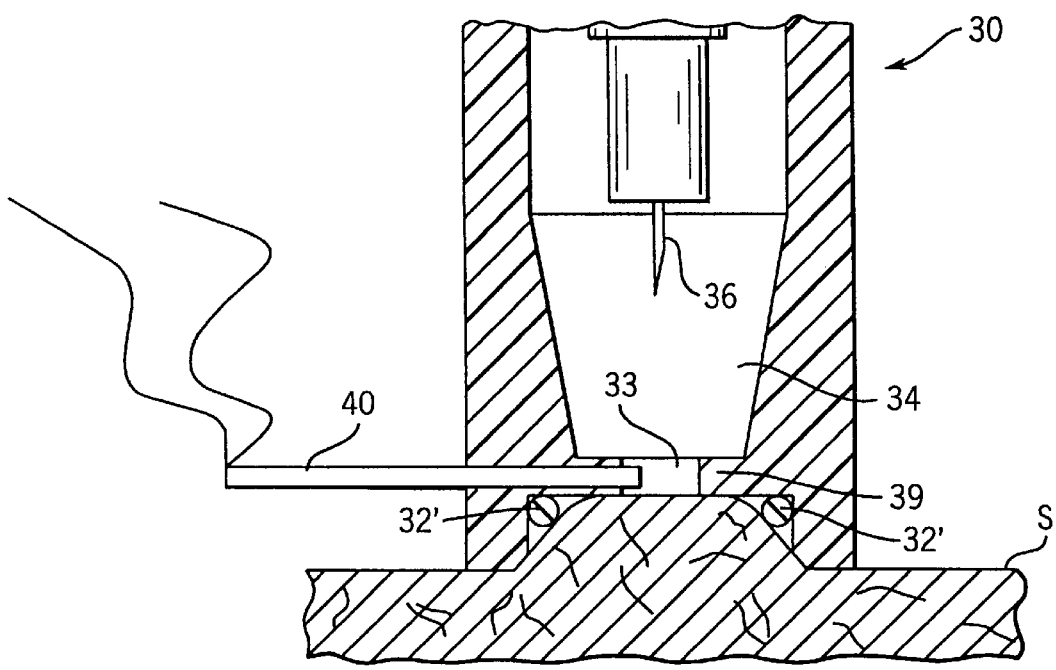
FIG. 4 is a schematic diagram illustrating an alternative seal for the vacuum of the device of the present invention.

Operation of the blood extraction device 10 will now be described. Referring now to FIGS. 1, 2 and 3, the nosepiece 30 of the lancing assembly 16 is applied to the surface of the skin, designated herein by the letter "S". The end of the nosepiece 30 that contacts the skin is equipped with a seal 32. The purpose of the seal 32 is to prevent air from leaking into blood extraction chamber 34, so that the vacuum pump 14 can provide sufficient suction action for increasing the availability of blood to the area of the skin from which the sample is to be extracted, stretching the skin, and extracting the sample of blood from the unobstructed opening in the skin. The seal 32 surrounds an opening 33 in the nosepiece 30. The opening 33 in the nosepiece allows communication between the surface of the skin and a blood extraction chamber 34 in the nosepiece 30. The seal 32 is preferably made of a rubber or an elastomeric material. FIG. 4 illustrates an alternative position for the seal 32. In FIG. 4, the seal is designated by the reference numeral 32'. The remaining parts of FIG. 4 are the same as those of FIG. 2, and, accordingly, retain the same reference numerals as were used in FIG. 2.

The switch 22 is actuated, typically by being pressed, thereby activating the electronics 20, which starts the vacuum pump 14. The vacuum pump 14 then provides a suction action. The suction action of the vacuum pump 14 causes the skin circumscribed by the seal 32 to become engorged with blood. Engorgement of the skin with blood is accompanied by a stretching of and rising up of the skin up to opening 33.

After an appropriate period of time, which is typically pre-set by the programmer of the electronics, the lancing assembly 16 is triggered, thereby causing the lancet 36 to penetrate the skin that has risen up to the opening 33 and that is engorged with blood. The lancet 36 is preferably triggered automatically, by a solenoid valve 38 that causes a vacuum-actuated piston (not shown) to trigger the lancet 36. The lancet 36 is then retracted, preferably automatically. Thereupon, the blood flows out of the unobstructed opening resulting from the lancet 36, and, aided by the vacuum generated by the vacuum pump 14, is collected. When sufficient blood has been collected or a pre-set time interval has passed, the electronics 20 causes the vacuum pump 14 to stop. The device 10 can then be removed from the surface of the skin after another solenoid valve (not shown because it is hidden under solenoid valve 38) is opened to vent the vacuum to allow ease of removal of the device from the surface of the skin. Solenoid valves suitable for use with the apparatus described herein are commercially available from The Lee Company, Essex, Conn. and have the part number LHDA0511111H.

The blood is preferably directly collected on the application zone of a glucose detector, e.g., a reflectance strip or biosensor. The blood can then be used as the sample for a determination of glucose concentration in blood. Alternatively, the blood can be collected by other collection devices, such as, for example, a capillary tube or absorbent paper.

The apparatus of the present invention can include a glucose detector for analyzing the blood sample extracted by the apparatus. Glucose detectors are well-known in the art. With respect to glucose monitoring, there are two major categories of glucose detectors—reflectometers and biosensors. Representative examples of reflectometers suitable for this invention are described in U.S. Pat. No. 4,627,445, incorporated herein by reference. Representative examples of biosensors suitable for this invention are described in U.S. Pat. No. 5,509,410, incorporated herein by reference.

The glucose detector is preferably disposed in the nosepiece 30 of the lancing assembly 16. The glucose detector must be located at a position sufficiently close to the site of blood extraction so that the quantity of extracted blood collected will be sufficient to carry out a standard glucose monitoring test. Typically, this distance will preferably be no more than 5 mm from the site of blood extraction, more preferably no more than 3 mm from the site of blood extraction, most preferably no more than 1 mm from the site of blood extraction. Care must be taken in the placement of the glucose detector so that the detector does not adversely affect the vacuum, when a vacuum is employed to aid in the extraction of blood. In addition, the glucose detector 40 should be modified, if necessary, so that the blood collected in the collection zone of the glucose detector is capable of being used to activate the glucose detector.

FIG. 2 also illustrates a manner for disposing a glucose detector 40 in the nosepiece 30 of the lancing assembly 16.

This invention provides numerous advantages over blood extraction devices of the prior art. Among these advantages are the following:

1. Ability to use parts of the body, other than the finger, as a site for the extraction of blood;

2. Reduction of pain by eliminating the need to lance the finger;

3. Increase in speed of collection of blood samples by means of pre-treatment comprising a combination of stretching of the skin in conjunction with heat or vacuum or both heat and vacuum;

4. Incorporation of glucose detector in apparatus for extracting the blood sample.

The following examples illustrate various features of the present invention but is not intended to in any way limit the scope of the invention as set forth in the claims. In the following examples, the term "pierce" and forms thereof and the term "puncture"" and forms thereof are used interchangeably.

EXAMPLES

Example 1

This example illustrates that greater volumes of blood can be extracted and collected by applying a vacuum, pulsed or continuous, after piercing than can be extracted and collected when no vacuum is applied. No vacuum was applied prior to piercing.

Each of four people had his forearm (dorsal forearm) punctured four times (at four different positions on the forearm) with a "BD ULTRA-FINE" lancet in a "MEDIS-ENSE" lancet assembly (Model no. 97101) at two different levels of vacuum (−2.5 psig and −5.0 psig) and for each different vacuum pulsing frequencies (0, 0.2, 0.8, 3.2, 12.8, 25, 100 hertz). The vacuum was applied with a pipette tip having a diameter of 8 mm ("RAININ RT-200"). Four control runs without a vacuum were also carried out (one puncture per person). A total of 60 punctures per person were carried out. Accordingly, it can be seen that a total of 240 runs were carried out.

The vacuum was applied for a duration of 30 seconds after puncturing. Blood was collected into capillary tubes. In the control runs, the samples were extracted and collected 30 seconds after puncturing. The amount of blood collected was determined by measuring the length of blood in the tubes. The percentage of collections in which the volume of blood collected exceeded 1.0 μL was calculated. Sensation of pain was also recorded. The following pain scores were used:

Pain of 1=person did not feel anything or not sure if anything was felt

Pain of 2=person felt definite prick, not as painful as piercing of finger by standard finger lancet Pain of 3=person felt definite pain, approximately equal to a piercing of finger by standard finger lancet Blood collection results are set forth in TABLE I.

TABLE I

| Frequency (hertz) | Average volume of blood sample collected at −2.5 psig ($\mu$L) | Percent of samples having >1 $\mu$L of blood collected at −2.5 psig | Average volume of blood sample collected at −5.0 psig ($\mu$L) | Percent of samples having >1 $\mu$L of blood collected at −5.0 psig |
|---|---|---|---|---|
| 0 (Continuous) | 1.6 | 69 | 3.1 | 94 |
| 0.2 | 1.1 | 44 | 3.0 | 94 |
| 0.8 | 1.1 | 63 |  | 75 |
| 3.2 | 1.5 | 56 | 3.8 | 75 |
| 12.8 | 1.8 | 75 | 3.1 | 100 |
| 25 | 2.3 | 75 | 3.2 | 94 |
| 100 | 2.4 | 81 | 2.7 | 88 |

With no vacuum, average volume of blood collected was 0.8 $\mu$L and 31% of the samples collected contained more than 1 $\mu$L. The pain results were as follows:

pain of 1=81%
pain of 2=17%
pain of 3=2%

The control runs (no vacuum) provided much lower volumes of blood collected than did the runs where vacuum was applied. Increased vacuum resulted in higher volumes of blood extracted. The pain was minimal, with only 2% of the punctures resulting in pain comparable to that resulting from a piercing of the finger.

Example 2

This example illustrates that application of vacuum prior to piercing as well as after piercing results in a greater volume of blood extracted than does the application of vacuum only after piercing.

Each of four people had his forearm (dorsal forearm, middle of forearm) punctured sixteen times (at sixteen different positions on the forearm) with a "BD ULTRA-FINE" lancet in a modified "MEDISENSE" lancet assembly at four different levels of vacuum. The four levels of vacuum used were −2.5, −5.0, −7.5, and −10.0 psig. The "MEDISENSE" lancet device was modified to allow vacuum to be pulled through the lancet assembly. Four punctures per person were carried out at each of the four levels of continuous vacuum. Accordingly, it can be seen that a total of 64 runs were carried out.

Prior to puncturing, the vacuum was applied for a period of 30 seconds; subsequent to puncturing, the vacuum was applied for a period of 30 seconds. The skin was under vacuum at the time the lancet was triggered. After the lancet was triggered, the lancet assembly was removed, and the vacuum was used to apply the same level of vacuum that had been used for the vacuum prior to puncturing. The vacuum, both prior to puncturing and subsequent to puncturing, was applied with a pipette tip having a diameter of 8 mm ("RAININ RT-200"). The pipette tip of the vacuum device was held level to the plane of the skin. Blood was then collected into capillary tubes. The amount of blood collected was determined by measuring the length of blood in the tubes. The percentage of collections in which the volume of blood collected exceeded 1.0 $\mu$L was calculated. Sensation of pain was also recorded. Blood collection results are set forth in TABLE II.

TABLE II

| Vacuum level (psig) | Average volume of blood sample collected ($\mu$L) | Percent of samples having >1 $\mu$L of blood collected |
|---|---|---|
| −2.5 | 4.6 | 94 |
| −5.0 | 7.8 | 100 |
| −7.5 | 9.2 | 100 |
| −10.0 | 14.0 | 100 |

The pain results were as follows:

pain of 1=58%
pain of 2=31%
pain of 3=11%

A nearly linear relationship between level of vacuum and volume of blood collected was observed. The average volume of blood collected with vacuum applied prior and after piercing was approximately twice that collected with vacuum applied only after piercing without vacuum applied prior to piercing. See the results of Example 1 for this comparison (7.8 $\mu$L vs. 3.1 $\mu$L). The volume of blood collected was always above 1 $\mu$L for all levels of vacuum, except −2.5 psig.

Example 3

This example illustrates that localized heating of the area to be pierced followed by vacuum after piercing results in a greater volume of blood being extracted than does extraction with only vacuum after piercing.

Each of four people had his forearm (dorsal forearm, middle of forearm) punctured eight times (at eight different positions on the forearm) with a "BD ULTRA-FINE" lancet in a "MEDISENSE" lancet assembly with heat applied (45° C.) prior to piercing for two different time periods, 15 seconds and 60 seconds. A total of 32 runs were carried out, 16 runs where the pre-heating duration was 15 seconds and 16 runs where the pre-heating duration was 60 seconds.

Heat was applied with a heating block, which was an aluminum block having a square face covered with a "KAPTON" film heater element controlled by an "OMEGA" DP41 temperature controller using a T-type thermocouple. Vacuum was applied after each puncturing for 30 seconds at −5.0 psig. Blood was collected into capillary tubes. The amount of blood collected was determined by measuring the length of blood in the tubes. The percentage of collections in which the volume of blood collected exceeded 1.0 $\mu$L was calculated. Pain was also tracked. Blood collection results are set forth in TABLE III.

TABLE III

| Pre-piercing heating duration (seconds) | Average volume of blood samples collected ($\mu$L) | Percent of samples having >1 $\mu$L of blood collected |
|---|---|---|
| 15 | 6.91 | 94 |
| 60 | 11.6 | 100 |

The pain results were as follows:

pain of 1=91%
pain of 2=9%
pain of 3=0%

The average volume of blood collected using a pre-heating duration of 15 seconds was more than twice the average volume of blood collected at a post-puncturing vacuum level of −5.0 psig., with no pre-heating. See the results of Example 1 for this comparison (6.91 µL vs. 3.1 µL). The average volume of blood collected using a pre-heating duration of 60 seconds was approximately four times the average volume of blood collected at a post-puncturing vacuum level of −5.0 psig, with no pre-heating. See the results of Example 1 for this comparison (11.6 µL vs. 3.1 µL).

Example 4

This example illustrates the effect that stretching the skin upwardly with a vacuum has on the extraction of blood.

Each of four people had his forearm (dorsal forearm, middle of forearm) punctured eight times (at eight different positions on the forearm) with a "BD ULTRA-FINE" lancet in a "MEDISENSE" lancet assembly. Vacuum was applied for a period of 30 seconds prior to puncturing at −5.0 psig using two different vacuum fixtures. The first fixture was a 15 mm diameter vacuum fixture (i.e., a hollow cylindrical tube) used without a net strung across the opening of the tube. The second fixture was a 15 mm diameter vacuum fixture (i.e., a hollow cylindrical tube) used with a net strung across the opening of the tube. The net prevented skin from being raised up into the vacuum fixture. The same vacuum fixture used prior to puncturing was applied for a period of 30 seconds after puncturing. The fixture was held level with the plane of the skin. Four punctures were carried out per person per condition (without net, with net). Accordingly, it can be seen that a total of 32 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE IV.

TABLE IV

| Net across nosepiece | Average volume of blood sample collected (µL) | Percent of samples having >1 µL of blood collected |
|---|---|---|
| No | 5.2 | 87 |
| Yes | 0.6 | 19 |

The pain results were as follows:
    pain of 1=94%
    pain of 2=6%
    pain of 3=0%

The magnitude of the difference in volume of blood collected and success rates (i.e., percent of samples having >1 µL of blood collected) between the condition of stretching the skin in combination with a vacuum and the condition of not stretching the skin in combination with a vacuum was unexpected. The pain scores were low. This example demonstrates that the combination of skin stretching and applied vacuum significantly increased the volume of blood extracted.

Example 5

This example illustrates the effect the area of the extraction site has on the volume of blood collected.

Each of four people had his forearm (dorsal forearm, middle of forearm) punctured at 32 different positions on the forearm with a "BD ULTRA-FINE" lancet in a modified "MEDISENSE" lancet assembly. The "MEDISENSE" lancet assmbly had been modified with a more powerful spring and a port had been added.

Vaccum was applied for less than five seconds prior to puncturing. The forearm was punctured under a vacuum of either −5.0 psig or −7.5 psig. The was maintained for 30 seconds after puncturing. The diameter used to apply vacuum after puncturing was varied, with diameters of 4, 6, 8, and 10 mm being used. Four punctures per condition (diamter, vaccum level) were carried out per person. Accordingly, it can be seen that a total of 128 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE VA and VB.

TABLE VA vacuum level = −5.0 psig

| Vacuum diameter (mm) | Average volume of blood sample collected (µL) | Percent of samples having >1 µL of blood collected |
|---|---|---|
| 4 | 0.3 | 0 |
| 6 | 1.7 | 69 |
| 8 | 3.4 | 94 |
| 10 | 4.1 | 100 |

TABLE VB vacuum level = −7.5 psig

| Vacuum diameter (mm) | Average volume of blood sample collected (µL) | Percent of samples having >1 µL of blood collected |
|---|---|---|
| 4 | 0.8 | 25 |
| 6 | 3.1 | 94 |
| 8 | 3.4 | 81 |
| 10 | 6.3 | 94 |

The pain results were as follows:
    pain of 1=89%
    pain of 2=10%
    pain of 3=1%

The volume of blood collected and success rates (i.e., percent of samples having >1 µL of blood collected) were found to vary directly with the area of skin raised up into the device by the vacuum. A much greater volume of skin was raised up into the larger diameter pipette tip than into the smaller diameter pipette tips.

Example 6

This example illustrates that a plastic multiple point lancet can be used with heat and vacuum to collect a useful amount of blood.

Each of four people had his forearm (dorsal forearm, middle of forearm) punctured sixteen times (at sixteen different positions on the forearm) with a Greer Derma PIK® System for allergy testing (Greer Laboratories, Inc., Lenoir, N.C. 28645) modified to fit into a "MEDISENSE" lancet assembly. Pre-heating was carried out at approximately 40° C. and 45° C. for 15 and 60 seconds prior to puncturing. Four punctures were carried out per condition (temperature, time) per person. Accordingly, it can be seen that a total of 64 runs were carried out.

Heat was applied with a heating block, which comprised an aluminum block having one face covered with a "KAPTON" film heater element controlled by an "OMEGA"

DP41 temperature controller using a T-type thermocouple and the opposite face in contact with the larger base of a frustum of a cone made of copper. The larger base of the frustum had a diameter of 0.50 in. The height of the frustum was 0.50 in. The smaller base of the frustum had a diameter of 0.35 in. The smaller base had a cylindrical opening having a diameter of 0.125 in. The cylindrical opening had a common axis with the frustum. The cylindrical opening reduced the heating surface of the copper frustum. Vacuum (−5.0 psig) was applied for a period of 30 seconds after puncturing. The vacuum in contact with the skin was formed by a pipette tip having a diameter of 8 mm. The pipette tip was held level with the plane of the skin. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE VI.

TABLE VI

| Temperature (° C.)/Time (seconds) | Average volume of blood sample collected (µL) | Percent of samples having >1 (µL) of blood collected |
| --- | --- | --- |
| 40/15 | 2.4 | 31 |
| 40/60 | 2.6 | 50 |
| 45/15 | 2.3 | 56 |
| 45/60 | 5.2 | 81 |

The pain results were as follows:
pain of 1=100%
pain of 2=0%
pain of 3=0%

This example demonstrates that a blood extraction process employing a multi-point plastic lancet, pre-piercing heating, skin stretching, and post-piercing vacuum can extract at least 1 µL of blood at least 50% of the time.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for obtaining a sample of blood for a diagnostic test, said method comprising the steps of:
   (a) forming an unobstructed opening in an area of skin from which said sample is to be extracted;
   (b) extracting said sample from said unobstructed opening in said area of said skin, with the aid of (1) a vacuum generated by a pump capable of being switched on and off to maintain a desired level of vacuum and (2) stretching of the skin, whereby sufficient blood is collected for said diagnostic test, further comprising the step of increasing the availability of blood to said area of said skin from which said sample is to be extracted prior to forming said opening in said area of said skin from which said sample is to be extracted.

2. The method of claim 1, wherein said diagnostic test is a test to determine the concentration of glucose in blood.

3. The method of claim 1, wherein a vacuum is used to increase the availability of blood to said area of said skin from which said sample is to be extracted prior to forming said opening in said area of said skin from which said sample is to be extracted.

4. The method of claim 3, wherein stretching is used to increase the availability of blood to said area of said skin from which said sample is to be extracted prior to forming said opening in said area of said skin from which said sample is to be extracted.

5. The method of claim 1, wherein heat is used to increase the availability of blood to said area of said skin from which said sample is to be extracted prior to forming said opening in said area of said skin from which said sample is to be extracted.

6. The method of claim 5, wherein heat is used to increase the availability of blood to said area of said skin from which said sample is to be extracted prior to forming said opening in said area of said skin from which said sample is to be extracted.

7. The method of claim 1, wherein said opening in said area of said skin from which the sample is to be extracted is formed by a lancet.

8. The method of claim 7, wherein said lancet penetrates said skin to a depth of no more than 1.6 mm.

9. The method of claim 1, wherein said extracted sample is analyzed by means of a glucose detector.

10. The method of claim 9, wherein said glucose detector employs a reflectometer.

11. The method of claim 9, wherein said glucose detector employs a biosensor.

12. The method of claim 1, wherein said opening in said area of said skin from which the sample is to be extracted is formed by a laser.

13. The method of claim 1, wherein said opening in said area of said skin from which the sample is to be extracted is formed by a fluid jet.

14. The method of claim 1, wherein said blood is obtained from a forearm.

15. A method for obtaining a sample of blood for a diagnostic test, said method comprising the steps of:
   (a) forming an unobstructed opening in an area of skin from which said sample is to be extracted;
   (b) extracting said sample from said unobstructed opening in said area of said skin, with the aid of (1) a vacuum generated by a pump capable of being switched on and off to maintain a desired level of vacuum and (2) stretching of the skin, whereby sufficient blood is collected for said diagnostic test, wherein said opening in said area of said skin from which the sample is to be extracted is formed by a lancet, wherein said lancet is cocked by means of a vacuum.

16. The method of claim 1, wherein said blood is obtained at a pain level lower than that experienced when a finger is pierced by a standard finger lancet.

17. A method for obtaining a sample of blood for a diagnostic test, said method comprising the steps of:
   (a) forming an unobstructed opening in an area of skin from which said sample is to be extracted;
   (b) extracting said sample from said unobstructed opening in said area of said skin, with the aid of (1) a vacuum generated by a pump capable of being switched on and off to maintain a desired level of vacuum and (2) stretching of the skin, whereby sufficient blood is collected for said diagnostic test, wherein said lancet is triggered by means of a vacuum.

18. An apparatus suitable for obtaining a sample of blood for analysis in a diagnostic test, said apparatus comprising:
   (a) a housing;
   (b) a device for forming an unobstructed opening in an area of skin from which the sample is to be extracted; and
   (c) a vacuum generated by a pump for extracting said sample from said unobstructed opening in said area of said skin, said housing further containing electronics having programmed instructions to switch the pump on and off to maintain a desired level of vacuum.

19. The apparatus of claim 18, further including a housing.

20. The apparatus of claim 18, wherein said device for forming said unobstructed opening comprises a lancet disposed in a lancing assembly.

21. The apparatus of claim 20, wherein said lancing assembly comprises a nosepiece having a seal, whereby a vacuum can be formed through the lancing assembly by said vacuum pump.

22. The apparatus of claim 21, wherein said vacuum is applied by a fixture having a major dimension ranging from about 2 mm to about 10 mm.

23. The apparatus of claim 18, wherein said lancet is capable of being retracted after it forms said unobstructed opening in said skin.

24. The apparatus of claim 18, wherein said device for forming said unobstructed opening is a laser.

25. The apparatus of claim 18, wherein said device for forming said unobstructed opening is a fluid jet.

26. The apparatus of claim 18, further comprising a heating element.

27. The apparatus of claim 18, further comprising a glucose detector.

28. The apparatus of claim 27, wherein said glucose detector is a biosensor.

29. The apparatus of claim 27, wherein said glucose detector is a reflectometer.

30. A method for obtaining a sample of blood for a diagnostic test, said method comprising the steps of:
   (a) forming an unobstructed opening in an area of skin from which said sample is to be extracted;
   (b) extracting said sample from said unobstructed opening in said area of said skin, with the aid of (1) a vacuum generated by a pump operated to maintain a desired level of vacuum and (2) stretching of the skin, whereby sufficient blood is collected for said diagnostic test, further comprising the step of increasing the availability of blood to said area of said skin from which said sample is to be extracted prior to forming said opening in said area of said skin from which said sample is to be extracted.

31. The method of claim 30, wherein said diagnostic test is a test to determine the concentration of glucose in blood.

32. The method of claim 30, wherein a vacuum is used to increase the availability of blood to said area of said skin from which said sample is to be extracted prior to forming said opening in said area of said skin from which said sample is to be extracted.

33. The method of claim 32, wherein stretching is used to increase the availability of blood to said area of said skin from which said sample is to be extracted prior to forming said opening in said area of said skin from which said sample is to be extracted.

34. The method of claim 30, wherein heat is used to increase the availability of blood to said area of said skin from which said sample is to be extracted prior to forming said opening in said area of said skin from which said sample is to be extracted.

35. The method of claim 34, wherein heat is used to increase the availability of blood to said area of said skin from which said sample is to be extracted prior to forming said opening in said area of said skin from which said sample is to be extracted.

36. The method of claim 30, wherein said opening in said area of said skin from which the sample is to be extracted is formed by a lancet.

37. The method of claim 36, wherein said lancet penetrates said skin to a depth of no more than 1.6 mm.

38. The method of claim 30, wherein said extracted sample is analyzed by means of a glucose detector.

39. The method of claim 38, wherein said glucose detector employs a reflectometer.

40. The method of claim 38, wherein said glucose detector employs a biosensor.

41. The method of claim 30, wherein said opening in said area of said skin from which the sample is to be extracted is formed by a laser.

42. The method of claim 30, wherein said opening in said area of said skin from which the sample is to be extracted is formed by a fluid jet.

43. The method of claim 30, wherein said blood is obtained from a forearm.

44. The method of claim 30, wherein said blood is obtained at a pain level lower than that experienced when a finger is pierced by a standard finger lancet.

45. A method for obtaining a sample of blood for a diagnostic test, said method comprising the steps of:
   (a) forming an unobstructed opening in an area of skin from which said sample is to be extracted:
   (b) extracting said sample from said unobstructed opening in said area of said skin, with the aid of (1) a vacuum generated by a pump operated to maintain a desired level of vacuum and (2) stretching of the skin, whereby sufficient blood is collected for said diagnostic test, wherein said opening in said area of said skin from which the sample is to be extracted is formed by a lancet, wherein said lancet is cocked by means of a vacuum.

46. A method for obtaining a sample of blood for a diagnostic test, said method comprising the steps of:
   (a) forming an unobstructed opening in an area of skin from which said sample is to be extracted;
   (b) extracting said sample from said unobstructed opening in said area of said skin, with the aid of (1) a vacuum generated by a pump operated to maintain a desired level of vacuum and (2) stretching of the skin, whereby sufficient blood is collected for said diagnostic test, wherein said lancet is triggered by means of a vacuum.

47. An apparatus suitable for obtaining a sample of blood through an area of skin for analysis in a diagnostic test, said apparatus comprising:
   (a) a device for forming an unobstructed opening in said area of said skin through which the sample is to be extracted;
   (b) a pump for generating a vacuum for extracting said sample from said unobstructed opening in said area of said skin, and
   (c) means for controlling said pump, wherein said means for controlling said pump operates said pump to maintain said vacuum at a specified level.

48. The apparatus of claim 47, further including a housing.

49. The apparatus of claim 47, wherein said device for forming said unobstructed opening comprises a lancet disposed in a lancing assembly.

50. The apparatus of claim 49, wherein said lancing assembly comprises a nosepiece having a seal, whereby a vacuum can be formed through the lancing assembly by said vacuum pump.

51. The apparatus of claim 50, wherein said vacuum is applied by a fixture having a major dimension ranging from about 2 mm to about 10 mm.

52. The apparatus of claim 47, wherein said lancet is capable of being retracted after it forms said unobstructed opening in said skin.

53. The apparatus of claim 47, wherein said device for forming said unobstructed opening is a laser.

54. The apparatus of claim 47, wherein said device for forming said unobstructed opening is a fluid jet.

55. The apparatus of claim 47, further comprising a heating element.

56. The apparatus of claim 47, further comprising a glucose detector.

57. The apparatus of claim 56, wherein said glucose detector is a biosensor.

58. The apparatus of claim 56, wherein said glucose detector is a reflectometer.

* * * * *